(12) United States Patent
Vukovic et al.

(10) Patent No.: US 11,179,540 B2
(45) Date of Patent: Nov. 23, 2021

(54) COGNITIVE ALERT SYSTEM

(71) Applicant: International Business Machines Corporation, Armonk, NY (US)

(72) Inventors: Maja Vukovic, New York, NY (US); Michael S. Gordon, Yorktown Heights, NY (US); Jinho Hwang, Ossining, NY (US); Ryan T. Gordon, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 87 days.

(21) Appl. No.: 16/050,804

(22) Filed: Jul. 31, 2018

(65) Prior Publication Data

US 2020/0038621 A1 Feb. 6, 2020

(51) Int. Cl.
*A61M 21/00* (2006.01)
*G04G 15/00* (2006.01)
(Continued)

(52) U.S. Cl.
CPC ........... *A61M 21/00* (2013.01); *A61B 5/4809* (2013.01); *A61B 5/4812* (2013.01); *G04G 15/006* (2013.01); *G04G 21/06* (2013.01); *G04G 99/006* (2013.01); *A61M 2021/0027* (2013.01); *A61M 2021/0083* (2013.01); *A61M 2205/52* (2013.01)

(58) Field of Classification Search
CPC .................. A61M 21/00; A61M 21/02; A61M 2021/0005; A61M 2021/0016; A61M 2021/0022; A61M 2021/0027; A61M 2021/0044; A61M 2021/0066; A61M 2021/0083
See application file for complete search history.

(56) References Cited

U.S. PATENT DOCUMENTS

| 7,967,739 B2* | 6/2011 | Auphan | A61B 5/08 |
| | | | 600/26 |
| 8,224,667 B1 | 7/2012 | Miller et al. | |

(Continued)

FOREIGN PATENT DOCUMENTS

CN 201477393 U 5/2010

OTHER PUBLICATIONS

IBM, "List of IBM Patents or Patent Applications Treated as Related," for U.S. Appl. No. 16/050,804, titled "Cognitive Alarm Clock," filed Jul. 31, 2018.

(Continued)

*Primary Examiner* — Carrie R Dorna
(74) *Attorney, Agent, or Firm* — Patterson + Sheridan, LLP

(57) ABSTRACT

Systems and methods to facilitate sleep are described. In on example, a cognitive alarm clock system for children learns sleep patterns and activities towards recommending sleep schedules and teaching independence. The system may detect the cognitive state of a child based on voice or cry pattern recognition, a time of day or night, scheduled activities, and social context, among other factors. The system may initiate actions to facilitate sleep in response to the cognitive factors. For example, the system may adjust lighting or push back a wakeup time. In another example, the system may use the cognitive analysis to teach children good sleeping habits by making recommendations to facilitate a good night's rest and encourage independence.

20 Claims, 6 Drawing Sheets

(51) Int. Cl.
    *G04G 99/00*     (2010.01)
    *G04G 21/06*     (2010.01)
    *A61B 5/00*     (2006.01)

(56) References Cited

U.S. PATENT DOCUMENTS

| | | |
|---|---|---|
| 8,493,220 B2 | 7/2013 | Virtanen et al. |
| 9,285,779 B2 | 3/2016 | Almudafier |
| 9,474,876 B1* | 10/2016 | Kahn .................... A61M 21/02 |
| 2003/0001727 A1 | 1/2003 | Steinmark |
| 2014/0067130 A1* | 3/2014 | Pillai ................... G06F 19/3418 |
| | | 700/275 |
| 2014/0253319 A1 | 9/2014 | Chang |
| 2017/0065792 A1* | 3/2017 | Bonvallet .............. G16H 50/50 |
| 2017/0258398 A1* | 9/2017 | Jackson ................. A61B 5/742 |
| 2018/0078198 A1* | 3/2018 | Reich .................... A61B 5/746 |

OTHER PUBLICATIONS

Liao et al., "iWakeUp: A Video-Based Alarm Clock for Smart Bedrooms," Journal of the Chinese Institute of Engineers, vol. 33., No. 5, pp. 661-668, 2010.

"New Alarm Clock is for Kids but it's the Parents Who are Sleeping in," PRNewswire, Jul. 31, 2008, available online www.americaninnovative.com.

* cited by examiner

COGNITIVE ALERT SYSTEM

FIELD OF THE DISCLOSURE

The present disclosure relates generally to computing technologies, and more particularly, to computer technologies that are used to manage sleep.

BACKGROUND

Good sleeping habits are important for health and well-being. Such habits are ideally formed at an early age to promote healthy sleep practices. Time demands, media distractions, poor diet, and other environmental factors can frustrate such efforts and lead to sleep deficits. Such deficits in sleep over time have been shown to have an escalating and long-term effect on brain function.

BRIEF SUMMARY

In a particular embodiment, an apparatus is disclosed that includes a cognitive detection module configured to learn cognitive information over time relating to a setting or a circumstance affecting sleep quality and a correlation module configured to correlate the cognitive information to a sleep cycle associated with a user. A recommendation module is configured to determine a recommendation relating to a schedule or an environmental factor to facilitate sleep based on at least one of the cognitive information and the sleep cycle, and an interface is used to communicate the recommendation to the user.

According to another implementation, a method of facilitating healthy sleep includes using machine learning to learn cognitive information over time relating to a setting or a circumstance affecting sleep quality, and to use a processor to correlate the cognitive information to a sleep cycle associated with a user. A recommendation relating to a schedule or environmental factors may be automatically determined to facilitate sleep based on at least one of the cognitive information and the sleep cycle, and the recommendation may be communicated to the user via an interface.

In another particular embodiment, a program product to facilitate healthy sleep includes a computer readable storage medium having computer readable program code embodied therewith, the computer readable program code being executable by a processor to learn cognitive information over time relating to a setting or a circumstance affecting sleep quality, to correlate the cognitive information to a sleep cycle associated with a user, to automatically determine a recommendation relating to a schedule or an environmental factor to facilitate sleep based on at least one of the cognitive information and the sleep cycle, and to communicate the recommendation to the user via an interface.

In a particular implementation, an apparatus includes a cognitive determination module configured to determine cognitive information relating to a setting or a circumstance impacting sleep of a user. A correlation module may be configured to determine an adjustment to at least one of a sleep schedule and an environmental factor based on the cognitive information. An interactive module configured to adjust at least one of the sleep schedule and the environmental factor based on the determined adjustment, wherein the interactive module is further configured to automatically adjust at least one of the sleep schedule and the environmental factor based on the determined adjustment. A teaching module configured to generate a recommendation explaining the adjustment, and an interface may be configured to communicate the recommendation to the user to teach sleeping independence.

In another example, a method of facilitating healthy sleep includes determining cognitive information relating to a setting or a circumstance impacting sleep of a user, determining an adjustment to at least one of a sleep schedule and an environmental factor based on the cognitive information; automatically adjusting at least one of the sleep schedule and the environmental factor based on the determined adjustment; generating an recommendation explaining the adjustment; and teaching sleep independence to the user by outputting the recommendation via an interface.

According to another particular embodiment, a program product to facilitate healthy sleep includes a computer readable storage medium having computer readable program code embodied therewith, the computer readable program code being executable by a processor to determine cognitive information relating to a setting or a circumstance impacting sleep of a user, to determine an adjustment to at least one of a sleep schedule and an environmental factor based on the cognitive information, to automatically adjust at least one of the sleep schedule and the environmental factor based on the determined adjustment, to generate an recommendation explaining the adjustment, and to teach sleep independence to the user by outputting the recommendation via an interface.

Features that characterize embodiments are set forth in the claims annexed hereto and forming a further part hereof. However, for a better understanding of the embodiments, and of the advantages and objectives attained through its use, reference should be made to the Drawings and to the accompanying descriptive matter in which there are described through exemplary embodiments.

DETAILED DESCRIPTION

Figure 1:
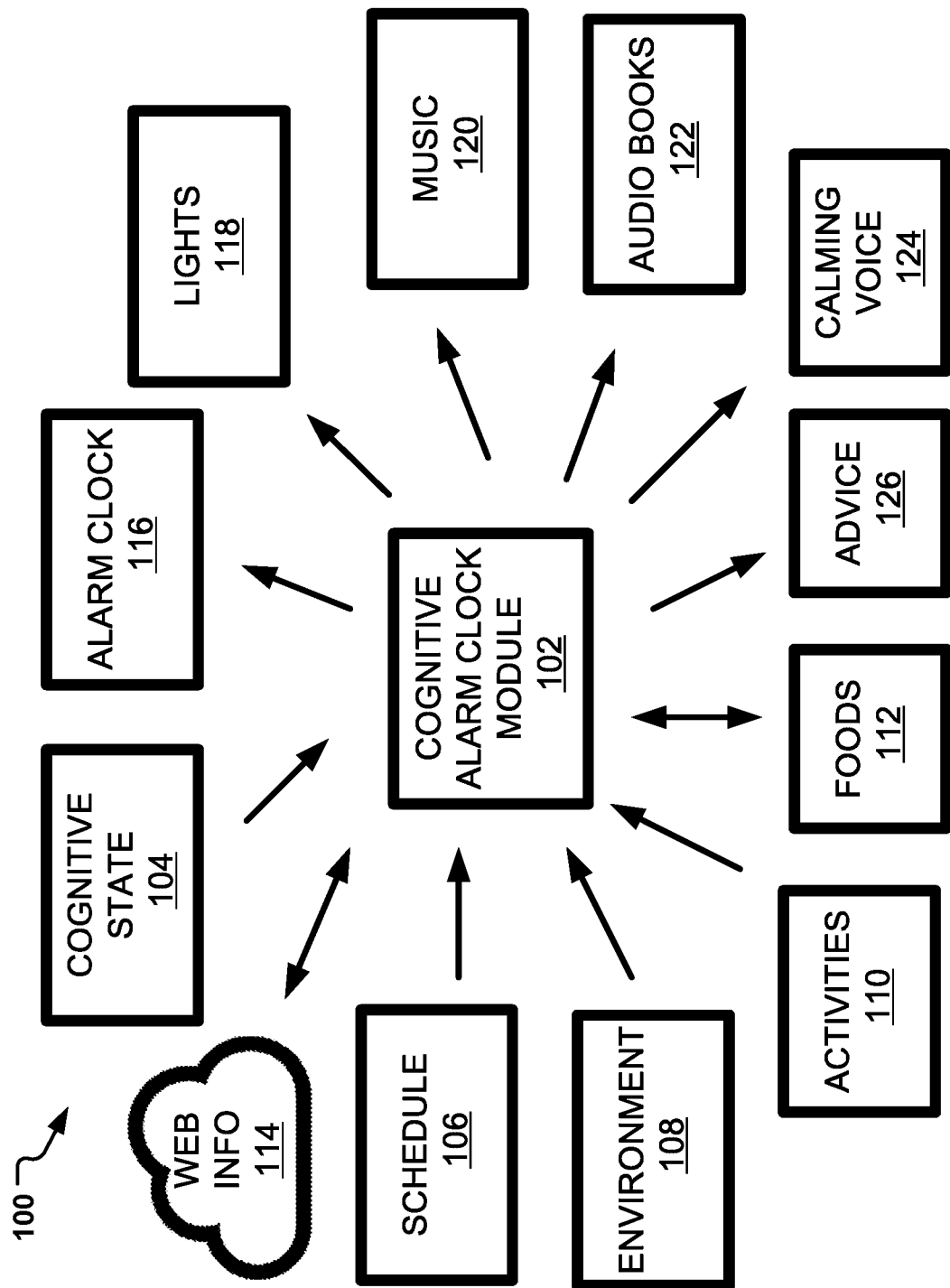
FIG. 1 shows a block diagram of a computing system in accordance with an embodiment.

According to a particular embodiment, a cognitive alarm clock system for children learns their sleep patterns and activities towards recommending sleep schedules and teaching independence. A module of the system may detect the cognitive state of a child based on voice or cry pattern recognition, a time of day or night, scheduled activities, and social context, among other factors. The system may initiate actions to facilitate sleep in response to the cognitive factors. For example, the system may adjust lighting or push back a wakeup time. In another example, the system may use the cognitive analysis to teach children good sleeping habits by making recommendations to facilitate a good night's rest and encourage independence.

Benefits of an embodiment of the cognitive alarm clock system allow children to sleep longer, and thus, have longer attention spans, higher IQs, and become less likely to experience hyperactivity. The system may be used with babies to make them less fitful and socially demanding by enabling them to better entertain and amuse themselves. Toddlers who get better sleep using an embodiment may be more fun to be around, more sociable, and less demanding. Healthy sleep enabled by an embodiment of the system positively affects neurologic development and appears to be the right treatment for the prevention of many learning and behavioral problems. When used with children having attention deficit hyperactivity disorder (ADHD), use of the system to improve sleep may dramatically improve peer relations and classroom performance. In this manner, an embodiment of the system may be used to optimize objectives that impact on the overall sleeping behaviors.

For example, an embodiment of the system may apply algorithms designed to determine a desired length of sleep (e.g. a sufficient amount of sleep). The system may execute program code to implement conditions and consider factors that affect a quality of sleep. For instance, what conditions may facilitate uninterrupted sleep. An output of the system may pertain to intermittent recovery. That is, the system may calculate a proper number of age-appropriate naps given certain conditions. Another output and consideration may regard a sleep schedule that is in synchronization with the natural biological rhythms. For instance, the program code may be used to determine an internal clock or circadian rhythm based on the age of a child. Depending on factors, such as age, the actions taken or recommended may be different.

In the case of facilitating sleep in newborns (e.g., aged under two months), the system may use a camera, a microphone, and a vibration sensor, among other equipment, to observe sleep patterns and identify signs of sleepiness. A speaker or digital readout may instruct a parent to put a baby in the crib when drowsy, rather than when already asleep. The system may instruct and monitor to make sure a baby is placed on their back with their face and head clear of blankets and other soft items. Such a recommendation may be provided to parents to avoid sudden infant death syndrome (SIDS). The system may encourage parents to enable nighttime sleep, while initiating additional action, such as playing soothing music.

In the case of infants (e.g., children aged between three and eleven months). The system may implement actions designed to develop regular daytime and bedtime schedules. The system may create a consistent and enjoyable bedtime routine by communicating to parents about times and other tips towards establishing a regular and sleep friendly environment. For example, the system educates parents when would be the ideal feeding or sleeping time during the night time. Also, the system and advice may encourage a baby to fall asleep independently and to learn self-soothing techniques.

Considerations for toddlers (e.g., between one and three years of age), may include output advice and alarm settings determined to maintain a daily sleep schedule and consistent bedtime routine. The system may take steps to help the bedroom environment be the same every night and throughout the night. The system may determine and communicate limits that are consistent, communicated and enforced. Where determined to be useful, an embodiment of the system will recommend use of a security object, such as a blanket or stuffed animal.

Preschoolers (e.g., three to five years of age) may have different sleep goals. An alarm clock of the system may help maintain a regular and consistent sleep schedule. The system can recommend a relaxing bedtime routine that ends in the room where the child sleeps. For instance, the system may encourage listening to a story or song. An embodiment of the system may encourage parents of a child to have the child sleep in the same sleeping environment every night, in a room that is cool, quiet and dark. For instance, the user may be discouraged from having a video or music playing in their room around bedtime. Similarly, the clock is aware of daylight savings and its impact on the kids' schedule and sleep patterns.

An embodiment may teach school-aged children (e.g., between 5 and twelve years of age) about healthy sleeping habits. The system may continue to emphasize a need for a regular and consistent sleep schedule and bedtime routine. The system may provide a sleep plan that is designed to make a bedroom conducive to sleep. For instance, a room may be kept dark, cool and quiet, without a computer, television, music player, or cellular phone. An embodiment of the system provides instructions on foods to avoid or try to help sleep. For instance, the system may have a child stay clear of caffeine.

In a preferred embodiment, an embodiment of a cognitive alarm clock may assess a current cognitive state of the person in the room with a clock. The cognitive state may be compared to a benchmark, or series of thresholds. For instance, an embodiment of a clock may respond to a troubled cognitive state of the child in the soothing voice of a parent or sibling. Put another way, if the clock detects that the child's movements or sounds exceed a context-aware threshold, the system may respond by telling the child to "calm down, and close your eyes," or "Go back to sleep." Further, the cognitive clock could sing a lullaby, or tell a story to the child to calm down the child or put them back to sleep. In another embodiment, when a preset alarm on the cognitive alarm clock rings, the clock could automatically reset the alarm (e.g., snooze or set a variable delay time until a next ring) depending on a calendar, schedule, appointments, school, or day-care arrangement of the child and/or a parent. An additional factor may include the quality of sleep the child had during the previous night.

An embodiment of an alarm clock system may be synchronized with a schedule and activities of a user. For instance, a processor may execute program code that identifies that a child must pack their lunch for a school field trip. The system may receive input indicating whether the lunch has been packed before morning, and if not, the alarm clock system may awaken the child earlier to start their day and provide additional time for the packing. In another example, the system may allow a user who has nothing scheduled to sleep later than a normal awakening time.

An embodiment of the system may monitor bodily functions to aid in sleep analysis. To this end, the system may include monitoring devices, such as an infrared sensor, a movement sensor, and a sound sensor. The infrared sensor may measure the body temperature of user, which is known to drop during sleep. The body temperature and time may be a useful data to have in determining the overall quality of a child's sleeping patterns. A microphone may be used to pick up breathing patterns of children while they sleep. During sleep, breathing patterns become regular, and by measuring these breathing patterns, the quality of sleep may also be monitored. Overall, by measuring bodily functions while sleeping, the quality of rapid eye movement (REM) sleep may be improved.

Predictive analytics may be used to detect and reason about the sleeping patterns, and anticipate possible difficulties, as well as to adjust the clock behavior. A risk management algorithm may assess the risk of a child's disturbed sleeping patterns, and if the risk is above certain threshold adjusts the clock behavior. (more examples) For example, the system may use machine learning from previous data and determinations. In one example, the system may recognize from stored data that a child is likely to need more rest during the evening of a day in which they have participated in a sporting event. In another example, the system also can understand the fatigue level from the body monitoring sensors. Accordingly, the system may recommend a warm drink or music known to help relax the child. A later wake time may be calculated to provide more REM for the child.

A sample risk/impact function may be mathematically represented by an illustrative equation: $R(\theta,\delta)=E_\theta L(\theta,\delta(X)) = \int_x L(\theta,\delta(X)) \, dP_\theta(X)$, where $\delta$ is a fixed (possibly, but not necessarily known) state of nature, and $X$ is a vector of observations stochastically drawn from a population. A population may include a list of soothing actions applied in the past, a child's health, and contextual state, among other data. $\theta$ may be the expectation overall population values of $X$, and $dP_\theta$ may be a probability measure over an event space of $X$, parametrized by $\delta$. The integral may be evaluated over an entire support of $X$.

According to a particular embodiment, a cognitive alarm clock system for children learns sleep patterns and activities towards recommending sleep schedules and teaching independence. A module of the system may detect the cognitive state of a child based on voice or cry pattern recognition, restlessness, a time of day or night, and social context. Social context may regard an immediate physical and social setting and occurrences in which the child lives.

A module of an embodiment of the system may learn effective ways of teaching children to be independent. For example, the system may encourage the child or may automatically play soothing music, read a book, and encourage the child to go back to sleep. An embodiment of the module may identify and base recommendations and other actions on surroundings, circumstances, and context. The system may correlate these identified and with sleeping patterns to increase sleep quality.

A particular implementation of the module recommends to the child appropriate actions and notifies parents if there are concerns. For example, the system may alert a child when bedtime is approaching so that they brush their teeth in time, or indicate that they should go to bed early because of an early morning commitment. A parent could be notified if a child is watching a video or listening to music that is not conducive to sleep.

The module may embed a schedule of a sleeper and link the schedule to the alarm function of the system. The schedule may further include those schedules of their sibling, parent, caregiver, or teammate, among others. Based on one or more calendar entries, the system may inform the sleeper if they should get up to prepare for activity, or whether they may continue sleeping. One or more modules may measure body metrics, such as a temperature of the sleeper, and their breathing pattern, to improve sleep quality. Other environmental metrics may also be received and used to influence or otherwise affect sleep or consciousness. For example, a level of lighting in a room (e.g., impacted by a window or hall light) may be measured and assessed. Noise from outside of a bedroom or from a television or headset may likewise affect sleep and be assessed.

The module may predict sleep patterns and mark the calendar of a caregiver with warnings and notifications of possible sleep disruption. In this manner, a child and her teacher or parent may use information about their sleep to scale back planned activities.

An embodiment of an intelligent clock may report on the cognitive conditions of a child and aid with their quality of sleep, as well as to encourage their independence. To this end, the system may set a time based attribute, in addition to a calendar entry and a quality of sleep. Such attributes may include consideration of a cognitive state of a sleeper, as well as their environment. The system may further provide feedback to improve the length and quality of sleep. An implementation of the system also learns the sleeping patterns of the child. The sleeping pattern may be determined automatically over the course of one or multiple nights. Actions, such as initiating the playing of soothing music or a prerecorded message from a parent may encourage a user to go back to sleep. The system may link to and access calendar information to dynamically adjust wakeup times, or to reset a time on an alarm clock function based on the determined sleep pattern, schedule demands, and based on a determination of whether the sleep was deep or shallow.

An implementation of the system may determine an optimal wakeup time. The system may analyze sleep patterns and reasons for restlessness in children as they sleep to provide responses to improve independence.

Turning more particularly to the drawings, FIG. 1 shows a block diagram of a computing environment 100, or apparatus, that includes a cognitive alarm clock module 102 that may allow children to have more a productive and restorative rest. To this end, the computing environment 100 includes stored and real-time information, software, and hardware that may be used in combination to determine and implement automated actions to educate and facilitate rest.

For example, the cognitive alarm clock module 102 may receive cognitive state data 104 from a stored source, as well as sensors relaying real-time information. For example, a microphone and audio processing software may be used to detect and analyze noises (e.g., breathing, crying, rustling) associated with a sleeping child. Other cognitive state data 104 may include social context, as well as a mood of the child (e.g., excited, calm, contented). Still other examples of cognitive input to the cognitive alarm clock module 102 may include the time of day, as well as other external factors affecting their attitude and level of comfort. For instance, whether a child is alone or in the same room as a sibling may impact sleep. A child who is traveling away from home may sleep differently than when at home. What a child eats may affect their mood, so dietary information may be processed by the cognitive alarm clock module 102.

Additional cognitive input to the cognitive alarm clock module 102 may include a schedule 106 of a child or other person, as well as any schedules of a parent or activities affecting the individual.

Environmental factors 108, such as external noise, smell, or lighting in a room may be provided to the cognitive alarm clock module 102. Other environmental factors 108 may include softness or texture of pillows and blankets.

Activity data 110 may be input to the cognitive alarm clock module 102. Such activity data may reflect sports or lessons attended by the child earlier that day, and could include reading and soccer, among others. Certain types of activity, as well as food and drink consumption may affect the potential tiredness of a person. For example, a child may benefit from more sleep because they participated in a soccer match. However, they might go to sleep more quickly. In another instance, caffeine in chocolate consumed before bedtime may call for an adjustment of a pre-sleep routine. As such, food consumption and dietary information 112 may be provided to the cognitive alarm clock module 102.

Some of the above information may be stored over time to allow the cognitive alarm clock module 102 to learn over time the sleeping and other behavioral attributes of a particular sleeper. Learning may refer to artificial intelligence that uses statistical techniques to progressively improve performance on a specific task with data, and without explicit programming. Additionally, the cognitive alarm clock module 102 may access Internet information 114 to supplement data received from other local sources. Such information 114 may relate to the medical records and additional scheduling (e.g., calendar) information of an individual, among other topics.

Based on its analysis, the cognitive alarm clock module 102 may automatically adjust an alarm clock 116. For example, the cognitive alarm clock module 102 may determine that a child needs additional sleep based on a detected and recorded restlessness of the prior evening and delay the sounding of a predetermined alarm time.

The cognitive alarm clock module 102 may control lighting 118 in a room based on its cognitive analysis. For instance, the cognitive alarm clock module 102 may dim lights as part of a pre-sleep routine or turn in them on in response to a sensed nightmare. In another application, the lights may gradually increase to help wake a child up in the morning.

Similar to the functionality of the lighting module 118, a music component 120 may be automatically controlled by the cognitive alarm clock module 102 based on cognitive and other factors that have been determined by the cognitive alarm clock module 102. Soothing music may be played automatically to calm a baby, and may be silenced once they are asleep. A calming voice 124 may be initiated in response to a child awakening in the middle of the night. The voice may include a prerecorded audio message from a parent or caregiver.

The cognitive alarm clock module 102 may initiate the playback of an audio book (e.g., a bedtime story) to help a child relax before sleep. The cognitive alarm clock module 102 may further provide advice 126 in the form of displayed text or audio intended to help teach children about the benefits of sleep and how to facilitate healthy sleep habits. The child may ultimately learn from the cognitive alarm clock module 102 how to become more independent (e.g., have good habits without adult supervision or the cognitive alarm clock module 102).

Figure 2:
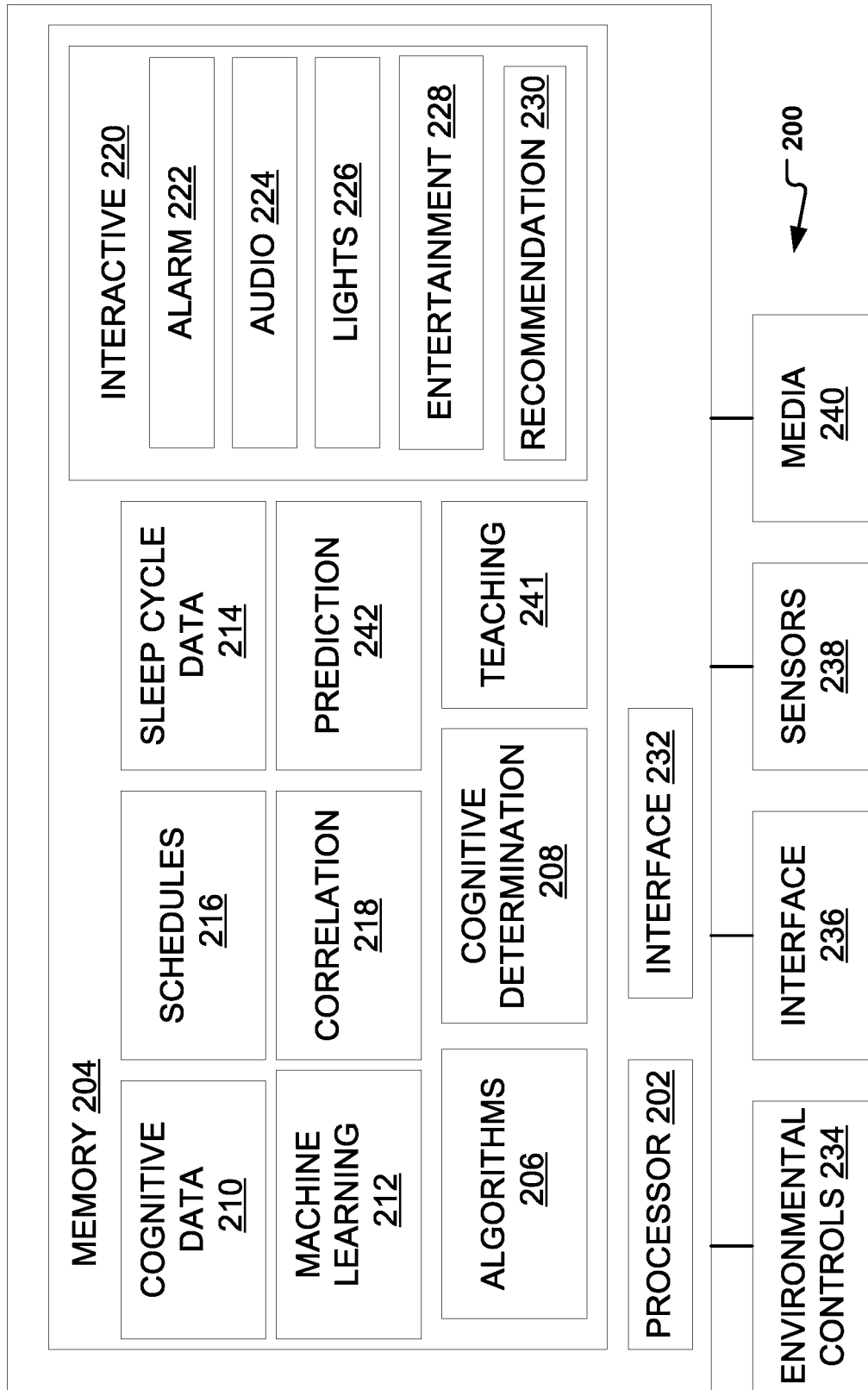
FIG. 2 is a block diagram showing components of a computing system configured to take action to encourage healthy sleep habits based in part on cognitive data.

FIG. 2 is a block diagram of another embodiment of a computing system 200, or apparatus, configured to promote healthy sleep and associated habits. They system 200 includes a processor 202 and a memory 204. The processor may access program code stored within the memory 204, such as algorithms 206, and the various other programmatic modules described herein.

For example, a cognition determination module 208 may be executed by the processor 202 to determine a cognitive state of a child. The resultant cognitive data 210 may be stored within memory 204 over time to enable machine learning module 212.

Similarly, sleep cycle data 214 may be detected and stored within the memory 204 over time. A correlation module 218 may execute algorithms having the cognitive data 210, the sleep cycle data 214, and scheduling data 216 to determine whether an action should be initiated using an interactive module 220. A prediction module 242 may include program code configured to anticipate and reduce sleep disturbances or to otherwise facilitate rest based on anticipated factors. A teaching module 241 may generate a recommendation explaining an action towards teaching sleep independence via the interactive module 220.

The interactive module 220 may allow the system to take an action to facilitate better rest and sleeping habits. For instance, the system 200 may adjust a wakeup time of an alarm 222. As explained herein, the system 200 may initiate music or soothing speech or other audio 224 where helpful using speakers or other media 240. Lighting controls 226 may be manipulated to create an optimal level of illumination, along with other environmental controls 234. A favorite video may be displayed, or an audio book played back using an interactive entertainment module 228 and media 240. The system may notify a caregiver about a sleeping disturbance or give advice to a user via a recommendation module 230 and interface 232.

Figure 3:
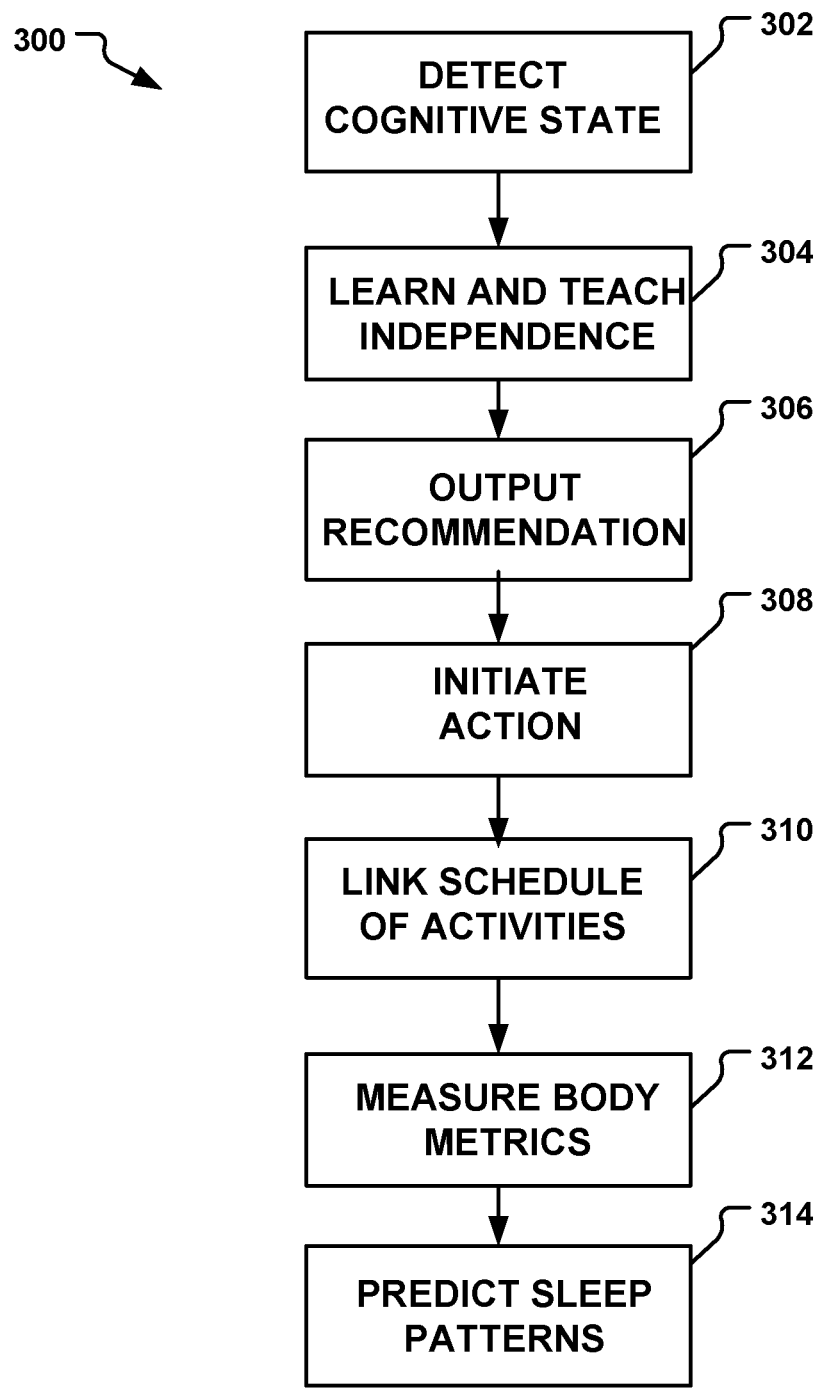
FIG. 3 is a flowchart that illustrates an embodiment of a method of promoting and facilitating productive rest using cognitive data.

FIG. 3 is a flowchart that illustrates an embodiment of a method 300 of using a cognitive alarm clock system that learns sleep patterns and activities. In one respect, the method 300 may recommend sleep schedules and teach independence. The method 300 may be performed by either of the embodiments of the systems 100, 200 of FIGS. 1 and 2.

A module of the system may detect at 302 a cognitive state of a child based on voice or cry pattern recognition, a time of day or night, and social context. As explained herein, social context may regard an immediate physical and social setting and occurrences in which a child lives. For instance, the system may consider a mood of a child, their activities, as well as sleep cycle information particular to the child as learned over time.

At 304, a module of the system may learn effective ways of teaching children to become independent. For example, the system may encourage the child to play soothing music, to read a book, or otherwise encourage the child to go back to sleep. Another or the same embodiment may initiate such actions automatically, depending on their age, experience, and needs of a child.

At 306, an embodiment of the module may identify and base recommendations and other actions on surroundings, circumstances, and context. The system may correlate these recommendations with sleep cycles, or patterns, to increase sleep quality. For instance, the system may use machine learning techniques to be able to match up and predict what the contextual data is likely to mean in terms of the REM or level of tiredness of the child. The system may recognize, in one example, that a child may need a nap or additional sleep following a camping trip, where they did not receive a full night's rest. The system may additionally figure in its determination the child has forgotten and is without their favorite pillow for the night.

In addition or in the alternative to a recommendation, a particular implementation of the module may initiate an action at 308 to help them sleep, and may notify parents if there are concerns. For example, the system may alert a child when bedtime is approaching so that they may brush their teeth in time, or that they should go to bed early because of an early morning commitment. In another example, a parent may be notified if a child is watching a web based movie or listening to music that is not conducive to sleep. If the system senses that an infant has awakened in the middle of the night, a recording of their parent's voice may be played back to reassure them.

The module may embed a schedule of a sleeper and link the schedule at 310 to the alarm function of the system. The schedule may further include those schedules of their sibling, parent, caregiver, or teammate, among others. Based on the calendar, the system may inform the sleeper if they should get up to prepare for activity, or whether they may continue sleeping. In this manner, the system may consider not only the scheduled activities of a user, but also cognitive information relating to their sleeping habits.

One or more modules may measure body metrics at 312, such as a temperature of the sleeper, and their breathing pattern, to improve sleep quality. Other environmental metrics may also be received and used to influence or otherwise affect sleep or consciousness. For example, a level of lighting in a room (e.g., impacted by a window or hall light) may be measured and assessed. Noise from outside of a bedroom or from a television or headset may likewise affect sleep and be assessed.

The module at 314 may predict sleep patterns and mark the calendar of a caregiver with warnings and notifications of possible sleep disruption of the child. For instance, the system may inform a parent that their child had a restless night without their usual and desired amount of deep sleep. Thus informed, her teacher or parent may use information about the child's prior night's sleep to scale back on planned activities.

Figure 4:
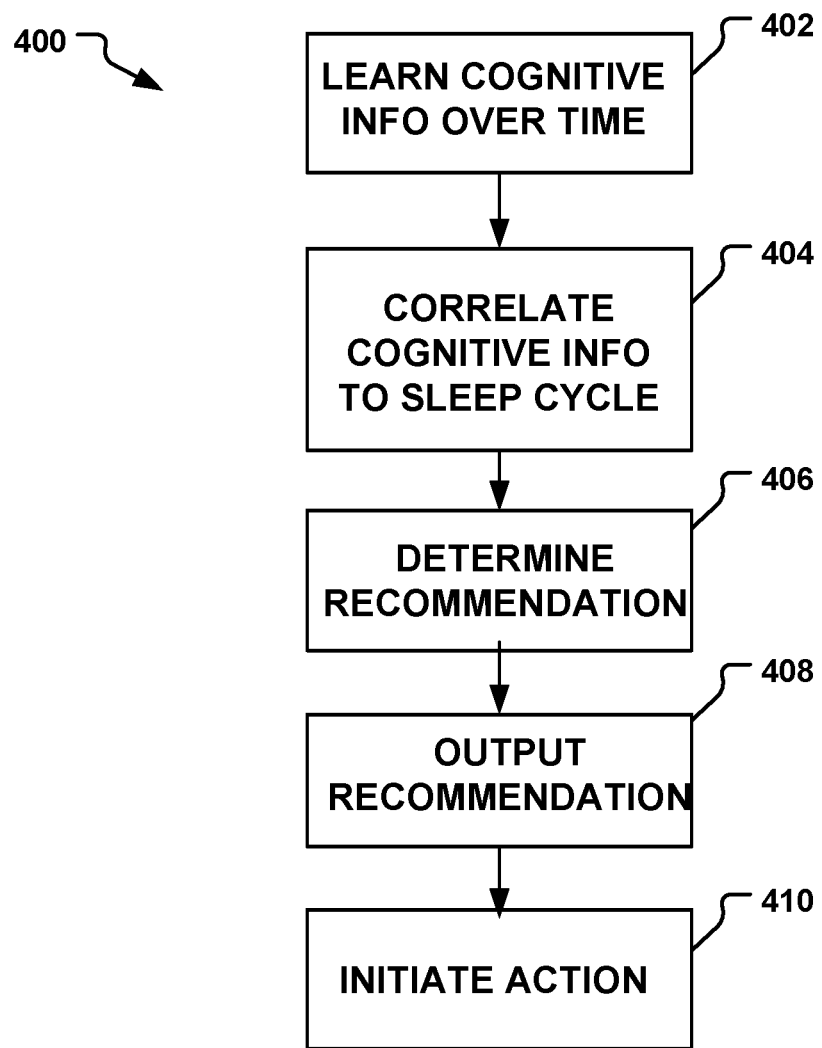
FIG. 4 is a flowchart that illustrates another embodiment of a method of facilitating sleep for a child.

FIG. 4 is a flowchart that illustrates an embodiment of a method 400 that initiates an action to facilitate sleep based on and in response to cognitive and other factors. At 402, the system may learn cognitive data. As explained herein, machine learning techniques may occur over a period of time to better understand and anticipate factors impacting sleep cycles for a particular person.

An embodiment of the system may correlate at 404 the cognitive state or information to known sleep cycles of the individual. By matching or otherwise assessing an impact on sleep, the system may determine an appropriate action, if desired to promote rest.

The system may determine and output a recommendation at 406 and 408. For instance, the system may produce audio suggesting that a child play soothing music or ask for warm milk to help relax and prepare them for bed.

Another or the same embodiment may initiate an action at 410 designed to facilitate sleep based on the detected cognitive and other factors. For instance, the system may play a lullaby or adjust an alarm based on the cognitive state of a child.

Figure 5:
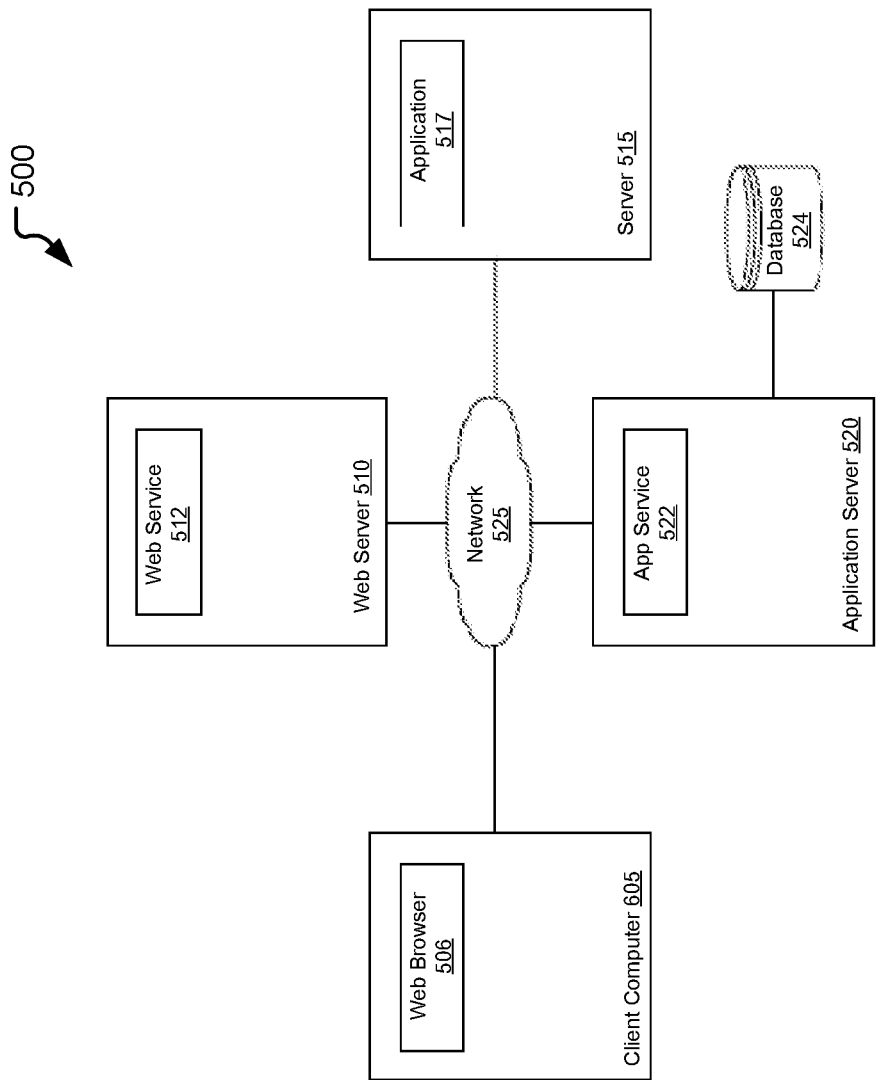
FIG. 5 illustrates another example computing system according to one embodiment, such as may be realized using a networked environment.

FIG. 5 illustrates another example computing system according to one embodiment, such as may be realized using a networked environment. As shown, the computing environment 500 includes a client computer 505, a web server 510, a server 515, and an application server 520. The client computer 505 may be a physical system (e.g., a desktop, laptop computer, mobile device, etc.) or a virtual computing instance executing in the cloud. The client computer 505 includes a web browser 507. A user may access data services through the web browser 507 over a network 525 (e.g., the Internet).

For instance, a user may access a web service 512 executing on a web server 510. In one embodiment, the web service 512 provides a web interface for an application server 520 (e.g., executing an application service 522). More specifically, the application service 522 provides a database 524. The database 524 may include data presented to users on the web browser 507.

Figure 6:
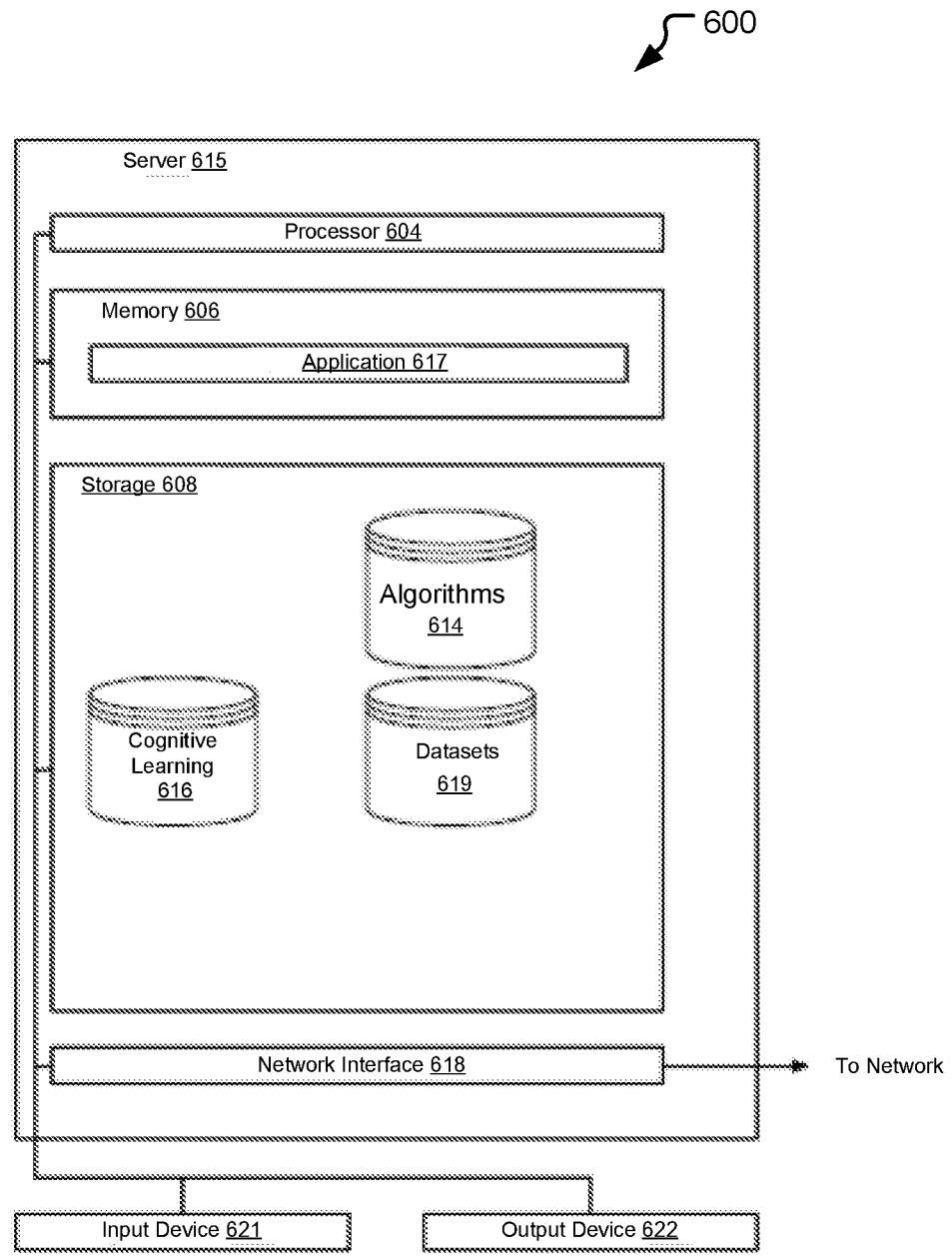
FIG. 6 further illustrates a server, such as the server of FIG. 5, according to one embodiment.

FIG. 6 further illustrates a server 615, such as the server 515 of FIG. 5, according to one embodiment. The server 615 generally includes a processor 604 connected via a bus to a memory 606, a network interface device 618, a storage 608, an input device 621, and an output device 624. The server 615 is generally under the control of an operating system. Examples of operating systems include the UNIX operating system, versions of the Microsoft Windows operating system, and distributions of the Linux operating system (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both). More generally, any operating system supporting the functions disclosed herein may be used. The processor 604 is included to be representative of a single CPU, multiple CPUs, a single CPU having multiple processing cores, and the like. Similarly, the memory 606 may be a random access memory. While the memory 606 is shown as a single identity, it should be understood that the memory 606 may comprise a plurality of modules, and that the memory 606 may exist at multiple levels, from high speed registers and caches to lower speed but larger DRAM chips. The network interface device 618 may be any type of network communications device allowing the navigation server 610 to communicate with other computers via the network 625.

The storage 608 may be a persistent storage device. Although the storage 608 is shown as a single unit, the storage 608 may be a combination of fixed and/or removable storage devices, such as fixed disc drives, solid state drives, removable memory cards, optical storage and network storage systems.

As shown, the memory 606 contains the application 617, which may be an application generally executed to take actions described herein. Storage 608 contains the algorithms 614, cognitive learning 616, and datasets 619.

The input device 621 may provide a keyboard and/or a mouse, etc. The output device 624 may be any conventional display screen. Although shown separately from the input device 621, the output device 624 and input device 621 may be combined. For example, a display screen with an integrated touch-screen may be used.

The system may introduce variations with alternatives for various words and concepts. Concept lists may be populated by the system to increase accuracy. The system may allow for the automatic expansion of the semantic space during graph creation. Elements may be automatically matched based on their semantic meaning during the graph query. The system may further adapt a word representation to the domain if needed by retraining the word representations. The system may use vocabulary automatically harvested from domain specific documents for clustering. The system may use the labels of these clusters as a way to automatically discover entity types for variation generation in the dialog system. The system may accomplish automatic creation and query matching, including the expansion and matching of triplets.

The system may automatically select cluster radii to focus results. An embodiment of the system may add a kernel that dissipates polynomially (e.g., one that is scaled with a small coefficient). The kernel may resolve instabilities in convergence of the algorithm. Regarding scaling of the kernel, the system may automatically increase or decrease the scaling factor based on how close to the highest possible mutual information that data is when the algorithm converges.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or related data available in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. An apparatus comprising:
    a cognitive determination module configured to determine cognitive information relating to a setting or a circumstance impacting a sleep cycle of a first organism;
    a correlation module configured to determine an adjustment to at least one of a sleep schedule and an environmental factor based on the cognitive information, a first schedule, and a second schedule, wherein the first schedule indicates a plan for daytime activities, and wherein the second schedule indicates a plan for upcoming daytime activities of a second organism;
    an interactive module configured to adjust at least one of the sleep schedule and the environmental factor based on the determined adjustment, wherein the interactive module is further configured to automatically adjust at least one of the sleep schedule and the environmental factor based on the determined adjustment;
    a teaching module configured to generate a recommendation explaining the adjustment; and
    an interface configured to communicate the recommendation to the first organism to teach sleeping independence and promote neurological development.

2. The apparatus of claim 1, wherein adjusting the sleep schedule includes adjusting a wakeup time.

3. The apparatus of claim 1, wherein the cognitive information includes learned sleep patterns and behaviors associated with the first organism.

4. The apparatus of claim 1, wherein the cognitive information is determined from sensing at least one of: breathing noises, vibrations, movement, temperature, and another body metric.

5. The apparatus of claim 1, wherein the recommendation is based on an age of the first organism.

6. The apparatus of claim 1, wherein the interactive module is further configured to generate a prediction relating to the cognitive information.

7. The apparatus of claim 1, wherein the cognitive information includes an internal clock or circadian rhythm based on an age of the first organism.

8. The apparatus of claim 1, wherein adjusting the environmental factor includes initiating at least one of: music, light adjustment, and voice playback.

9. The apparatus of claim 1, wherein the cognitive information relates to at least one of: a surrounding, a schedule, an occurrence, and a context relating to the first organism.

10. A method of facilitating healthy sleep, the method comprising:
    determining, via a cognitive alarm clock system, cognitive information relating to a setting or a circumstance impacting a sleep cycle of a first organism;
    determining, via the cognitive alarm clock system, an adjustment to at least one of a sleep schedule and an environmental factor based on the cognitive information, a first schedule, and a second schedule, wherein the first schedule indicates a plan for daytime activities, and wherein the second schedule indicates a plan for upcoming daytime activities of a second organism;
    automatically adjusting, via a cognitive alarm clock system, at least one of the sleep schedule and the environmental factor based on the determined adjustment;
    generating, via the cognitive alarm clock system, a recommendation explaining the adjustment; and
    teaching, via the cognitive alarm clock system, sleep independence and promoting neurological development by outputting the recommendation to the first organism.

11. The method of claim 10, further comprising generating, via the cognitive alarm clock system, a prediction relating to the cognitive information.

12. The method of claim 10, wherein adjusting the sleep schedule further comprises adjusting, via the cognitive alarm clock system, a wakeup time.

13. The method of claim 10, wherein adjusting the environmental factor includes adjusting, via the cognitive alarm clock system, at least one of: music, light adjustment, and voice playback.

14. The method of claim 10, further comprising adjusting, via the cognitive alarm clock system, a wakeup time based on a schedule of a third party.

15. The method of claim 10, further comprising determining, via the cognitive alarm clock system, the cognitive information using at least one of: a camera, a thermometer, a microphone, and a vibration sensor.

16. The method of claim 10, further comprising determining, via the cognitive alarm clock system, an internal clock or circadian rhythm based on an age of the first organism.

17. The method of claim 10, further comprising adjusting, via the cognitive alarm clock system, one of: music, a light, voice playback, and an alarm.

18. The method of claim 10, further comprising generating, via the cognitive alarm clock system, the recommendation based on at least one of: a surrounding, a schedule, an occurrence, and a context relating to the first organism.

19. The method of claim 10, wherein the adjustment is further determined based on a quality or texture of a sleeping aid, wherein the quality or texture of the sleeping aid comprises a softness or texture of a pillow or blanket.

20. A non-transitive program product to facilitate healthy sleep, the program product comprising:
a computer readable storage medium having computer readable program code embodied therewith, the computer readable program code being executable by a processor to determine cognitive information relating to a setting or a circumstance impacting a sleep cycle of a first organism, to determine an adjustment to at least one of a sleep schedule and an environmental factor based on the cognitive information, a first schedule, and a second schedule, wherein the first schedule indicates a plan for daytime activities, and wherein the second schedule indicates a plan for upcoming daytime activities of a second organism, to automatically adjust at least one of the sleep schedule and the environmental factor based on the determined adjustment, to generate a recommendation explaining the adjustment, and to teach sleep independence and promote neurological development by outputting the recommendation via an interface to the first organism.

* * * * *